United States Patent
Chida et al.

[11] Patent Number: 5,916,797
[45] Date of Patent: Jun. 29, 1999

[54] MUTANT STRAIN OF *TRICHOSPORONOIDES OEDOCEPHALIS*

[75] Inventors: Saburo Chida, Kitamoto; Toshiro Ochiai, Kasukabe, both of Japan

[73] Assignee: Nikken Chemicals Co., Ltd., Tokyo, Japan

[21] Appl. No.: 09/091,377

[22] PCT Filed: Jan. 17, 1997

[86] PCT No.: PCT/JP97/00077

§ 371 Date: Jun. 17, 1998

§ 102(e) Date: Jun. 17, 1998

[87] PCT Pub. No.: WO97/26323

PCT Pub. Date: Jul. 24, 1997

[30] Foreign Application Priority Data

Jan. 19, 1996 [JP] Japan ................................. 8-024901
Aug. 15, 1996 [JP] Japan ................................. 8-232641

[51] Int. Cl.⁶ ................................. C12N 1/14; C12P 7/18
[52] U.S. Cl. ........................................ 435/255.1; 435/158
[58] Field of Search .................................. 435/158, 255.1

[56] References Cited

PUBLICATIONS

Biotech. Lett. 15 (4) Marina et al "Microbial Transformation of Sucrose and Glucose to erythritol" pp. 383–388, 1993.
Can. J. Botany 45 (1967) Haskins et al "*Trichosporonoides Oedocephalis* N.Gen. N. Sp." pp. 515–520, 1967.
Biosci. Biotech. Biochem 60 (11) (1996) Park et al "Biochemical Characteristics of Osmophilic Yeasts Isolated from Pollens and Honey" pp. 1872–1873, 1996.

*Primary Examiner*—Herbert J. Lilling
*Attorney, Agent, or Firm*—Frishauf, Holtz, Goodman, Langer & Chick, P.C.

[57] ABSTRACT

A mutant strain of *Trichosporonoides oedocephalis* whose saccharide-based erythritol yield, at a saccharide concentration of 30 w/v % or higher, but less than 60 w/v %, is higher than that in its parent strain and whose cell biomass cultured is less than that of its parent strain.

2 Claims, No Drawings

MUTANT STRAIN OF *TRICHOSPORONOIDES OEDOCEPHALIS*

TECHNICAL FIELD

The present invention relates to a variant having a high erythritol producing ability and to a method for producing erythritol.

BACKGROUND ART

Two microorganisms, namely, *Moniliella tomentosa* var. *pollinis* CBS461.67 and Aureobasidium sp. SN-G42 FERM P-8940, are known currently to be employed practically to produce erythritol.

The former is employed, for example, in methods for producing polyols in an industrial scale by means of fermentation of saccharides (Japanese Patent Publication No. 6-30591 (30591/1994), ibid. 6-30592 (30592/1994), ibid. 6-30593 (30593/1994), ibid. 6-30594 (30594/1994)), and in these publications methods for producing a series of polyols including erythritol are disclosed.

However, the strain of *Moniliella tomentosa* var. *pollinis* employed in such methods has a poor saccharide resistance and suffers from reduced yield of erythritol at a high saccharide concentration. Thus, at the saccharide concentration of 25 w/v % the saccharide-based erythritol yield (amount of erythritol produced relative to the amount of saccharide consumed) is as high as 42%, but at the saccharide concentration as high as 35 w/v % the saccharide-based erythritol yield is 33%, and at 40 w/v % the yield is as markedly low as 27%.

On the other hand, the latter is disclosed in Japanese Patent Publications 4-11189 (11189/1992) and ibid. 4-635 (635/1992) in which a microorganism having an erythritol producing ability and a method for producing erythritol by means of fermentation using such microorganism are described.

The microorganism employed in such method has an excellent saccharide resistance and an excellent erythritol producing ability. However, since this strain exhibits extensive growth, separation of the cells from the fermentation fluid in the process of purification of erythritol in an attempt to conduct a mass production requires a prolonged period of time and resulting large amount of waste cells can not easily be disposed.

*Trichosporonoides oedocephalis* employed in the present invention was reported by R. H. Haskins (Canadian Journal of Botany, Volume 45, p. 515–520, 1967) with regard to its microbiological characteristics and its ability of producing erythritol. However, this report contained no description of the yield of erythritol.

In addition, a microorganism belonging to genus Trichosporonoides was reported by Marina A. Y. Aoki in Campinus University in Brazil (Biotechnology Letters, Volume 15, No.4, p.383–388, April 1993) to be employed in conversion from sucrose and glucose to erythritol, although the species is not known. According to this report, the rates of conversion from glucose to erythritol and sucrose to erythritol were as relatively high as 43.0% and 37.4%, respectively, but the saccharide concentration for such yields was as low as 10 w/v %, indicating a poor applicability to a production in an industrial scale.

DISCLOSURE OF THE INVENTION

An objective of the present invention is to provide a variant of *Trichosporonoides oedocephalis* having a high erythritol producing ability as well as a method for producing erythritol suitable for production in an industrial scale.

The first aspect of the present invention relates to a variant of *Trichosporonoides oedocephalis* whose saccharide-based erythritol yield at a saccharide concentration of 30 w/v % or higher but less than 60 w/v % is higher than that in its parent strain and whose cell biomass cultured is less than that of its parent strain.

The second aspect of the present invention relates to a method for producing erythritol comprising cultivating a strain of *Trichosporonoides oedocephalis* in a culture medium containing 20 to 50 w/v % of saccharides and then recovering the erythritol accumulated in the culture medium.

PREFERRED EMBODIMENTS OF THE INVENTION

An example of the variant of *Trichosporonoides oedocephalis* whose saccharide-based erythritol yield is higher and whose cell biomass cultured is smaller when compared with its parent strain as mentioned above is *Trichosporonoides oedocephalis* TO-241-14 strain (FERM BP-5773).

Examples of the strains employed in the method for producing erythritol suitable in an industrial scale production are the variant mentioned above as well as its parent strain, namely, *Trichosporonoides oedocephalis* (CBS649.66).

The inventive variant *Trichosporonoides oedocephalis* TO-241-14 strain (FERM BP-5773) can be obtained by treating the parent strain by a standard mutating method, such as physical mutating methods such as ultraviolet irradiation and radioactive irradiation as well as chemical mutating methods such as treatment with ethyl methanesulfonic acid, nitrosoguanidine and the like followed by screening from the variants obtained a strain whose cell density (turbidity) in culture medium is low and whose saccharide-based erythritol yield is high.

The bacteriological characteristics of a variant according to the present invention *Trichosporonoides oedocephalis* TO-241-14 strain (FERM BP-5773) are described below in relation with those of its parent strain (CBS649.66).

1. Morphological characteristics (1) Cells were incubated in YM medium at 25° C. for 3 days and then observed by a microscope.

|  | Variant | Parent strain |
|---|---|---|
| a) Shape: | Egg-like round shape to oval shape | Egg-like round shape to oval shape |
| b) Length: | 5 to 12.5 μm | 5 to 12 μm |
| Width: | 2.5 to 7 μm | 2 to 5 μm |

(2) Cells were incubated in yeast extract medium (containing 30% glucose and 1% yeast extract) at 35° C. for 3 days and then observed by a microscope.

|  | Variant | Parent strain |
|---|---|---|
| a) Shape: | Egg-like round shape to oval shape | Egg-like round shape to oval shape |
| b) Length: | 5 to 22.5 μm | 2.5 to 16 μm |
| Width: | 2.5 to 12.5 μm | 2.5 to 5 μm |

(Variants are mostly larger in shape than their parent strains.)

2. Mode of proliferation: Germination
   (Similar to the parent strain)

3. Physiological characteristics
  a) Fermentation of saccharides
  Wickerham's carbon compound anabolism test medium (Difco) was dispensed to tubes containing Durham's tubes, which were incubated at 25° C. for 3 weeks and then evaluated for evolved carbonate gas.

| D-Glucose | + | D-Galactose | + | Maltose | + |
| Sucrose | + | Lactose | − | Raffinose | − |

(Saccharides listed above were fermented similarly as in the parent strain.)

b) Assimilation of saccharides
  Wickerham's carbon compound anabolism test medium (Difco) was used in incubation at 25° C. for 3 weeks and then the culture was examined for cell growth based on turbidity.

| D-Arabinose | − | L-Arabinose | + | D-Ribose | + |
| D-Xylose | − | D-Glucose | + | D-Galactose | + |
| L-Rhamnose | − | D-Fructose | + | L-Sorbose | − |
| Maltose | + | Sucrose | + | Lactose | + |
| Cellobiose | + | Trehalose | + | Raffinose | − |
| Melezitose | − | Soluble starch | − | | |
| a-methyl-D-glycoside | − | Inosit | − | | |
| Erythritol | + | Salicin | − | | |
| D-mannitol | + | | | | |
| Glycerin | + | | | | |

(Saccharides listed above were fermented similarly as in the parent strain.)

| | Variant | Parent strain |
| --- | --- | --- |
| c) Assimilation of nitrate | + | + |
| d) Urease activity | + | + |
| e) Osmotic pressure resistance NaCl concentration | | |
| 14% | + | + |
| 16% | ± | + |
| 18% | − | + |
| Glucose concentration 60% | + | + |
| f) Growth range | | |
| (pH) | 2.5 to 9.0 | 2.5 to 9.5 |
| (Temp.) | 12 to 39° C. | 10 to 39° C. |
| g) Optimum growth condition | | |
| (pH) | 4.5 to 7.0 | 5.5 to 8.0 |
| (Temp.) | 25 to 30° C. | 25 to 30° C. |

As described above, while an inventive variant *Trichosporonoides oedocephalis* TO-241-14 strain has bacteriological characteristics analogous to those of the parent strain, it exhibits difference in morphological characteristics (size), pH and temperature ranges for growth and pH for optimum growth.

When erythritol is produced by fermentation, the inventive variant also exhibits difference from its parent strain as a result of its higher saccharide resistance, higher erythritol yield and smaller cell mass produced when compared with its parent strain.

Accordingly, we recognize the inventive strain as a novel bacterial strain, and designated as *Trichosporonoides oedocephalis* TO-241-14. This strain has been deposited to National Institute of Bioscience and Human-Technology Agency of Industrial Science and Technology, 1–3, mutant strain Higashi 1-chome, Tsukuba-shi, Ibaraki-ken, Japan on Dec. 12, 1996 in compliance with Budapest Treaty on the international recognition of the deposit of microorganisms under the acceptance number of FERM BP-5773 (transferred from Japanese original deposition, Japanese original deposit number: FERM P-15309, original deposited date: Nov. 24, 1995).

The method for cultivating a strain of *Trichosporonoides oedocephalis* and the method for producing erythritol employing this strain are described below.

The strain is cultivated aerobically in a liquid medium containing carbon source, nitrogen source, inorganic salts, etc.

The carbon source may be saccharides such as glucose, fructose, sucrose and maltose and starch-saccharified liquor containing these saccharides as well as carbohydrates such as sweet potato syrup and beet syrup, which may be employed independently or in combination. Among them glucose and sucrose can be used preferably.

The nitrogen source may be nitrogen compounds capable of being utilized by said microorganism, such as yeast extract, peptone, malt extract, corn steep liquor, aqueous ammonia, ammonium salts, urea, nitrates, which may be employed independently or in combination.

The inorganic salts may be phosphates, magnesium salts, calcium salts, potassium salts, iron salts, manganese salts and the like.

The cultivation is conducted by inoculating a liquid medium containing saccharides at a concentration of 20 to 60 w/v %, preferably 30 to 50 w/v % formulated as described above directly with the strain or with a seed inoculant culture obtained by pre-incubation followed by cultivation usually at pH 2.5 to 9.0, preferably at 3.0 to 4.0, at a temperature of 27 to 40° C., preferably at 35 to 39° C., usually for a period of 3 to 11 days.

Preferably, the cultivation is terminated at a time point when the maximum utilization of the nutrient sources in the medium and the maximum production of erythritol in the culture medium are achieved.

Erythritol accumulated in the culture medium is separated and recovered from the culture medium by a standard manner. For example, the cells are removed from the culture medium by filtration or centrifugation and then subjected to an appropriate combination of ion exchange resin treatment, adsorption chromatography, solvent extraction, concentration, crystallization and the like. In addition, decoloration with activated carbon and recrystallization employed usually may also be conducted for the purpose of removing impurities.

EXAMPLES

The present invention is further illustrated in the following examples which are not intended to restrict the scope of the invention. Example 1 (Acquisition of variant)

*Trichosporonoides oedocephalis* (CBS649.66) strain was inoculated to an yeast extract medium (containing 30 w/v % of glucose and 1 w/v % of yeast extract) and cultivated at 35° C. for 3 days while shaking. Then the culture fluid was subjected to 10-fold dilution with 1/15 M phosphate buffer (pH5.0) and irradiated with 15 W ultraviolet lump placed at the distance of 33 cm for 30 minutes while stirring gently in a petri dish.

Subsequently, the UV irradiated culture fluid was inoculated to an yeast extract medium, cultivated at 35° C. for overnight (18 hours) to fix the variation, and then applied as a smear onto an yeast extract agar plate (containing 30 w/v % of glucose, 1 w/v % of yeast extract and 1.5 w/v % of agar), which was cultivated at 27° C. for 5 days.

The colonies formed were harvested and separated, and then inoculated to 3 ml of an yeast extract medium which had previously been dispensed in a medium-sized tube (18×180 mm), which was then cultivated while shaking at 35° C. for 7 days.

Subsequently, the culture fluid obtained as described above was examined for the degree of proliferation by means of determining the turbidity of the culture fluid, i.e., by measuring the absorbance at 660 nm using a spectrophotometer (manufactured by Shimadzu, Model UV-2200). The saccharide-based erythritol yield after cultivation was calculated by determining the amounts of glucose remained and erythritol produced in the culture fluid using high performance liquid chromatography (Shimadzu, Model LC-9A).

Thus, a variant exhibiting a low turbidity of the culture fluid and having a high saccharide-based erythritol yield, namely, TO-241-14 strain (FERM BP-5773), was screened.

EXAMPLE 2

The variant (FERM BP-5773) obtained in Example 1 was inoculated to 40 ml of an yeast extract medium (containing 30 w/v % of glucose and 1 w/v % of yeast extract) and cultivated at 35° C. for 3 days while shaking. Then 3 ml (0.2% based on the volume of the medium) of the culture fluid obtained was inoculated to 1.5 liters of an yeast extract medium (containing 40 w/v % of glucose and 1.3 w/v % of yeast extract) and cultivated in a mini-jar fermenter (ABLE Co. Ltd., Model DPC-2) at 35° C. while stirring at 450 rpm at pH 4 for 7 days.

After termination of the cultivation, erythritol in the culture fluid was determined and the saccharide-based yield was 47.0%.

Subsequently, a 250 ml aliquot of this culture fluid was filtrated to remove the cell and the supernatant obtained was subjected to decoloration with activated carbon and desalting on an ion exchange resin (Mitsubishi Chemical Co. Ltd., SK-1B, PA-408) to obtain an effluent, which was concentrated to a saccharide concentration of 50% or higher and then cooled slowly to yield a crystal of erythritol.

IR absorption spectrum, melting point and nuclear magnetic resonance spectrum of the crystal obtained were compared with those of a standard erythritol, and were found to be identical, thus confirming the substance as erythritol.

EXAMPLE 3
(Comparison of cultivation temperature, turbidity and yield of erythritol)

The inventive variant (FERM BP-5773) and its parent strain (CBS649.66) were compared with regard to proliferation (as turbidity of the culture fluid) and saccharide-based erythritol yield (yield based on glucose consumed).

Each strain was inoculated to an yeast extract medium (containing 30 w/v % of glucose and 1 w/v % of yeast extract) and cultivated at 35° C. for 3 days while shaking. The culture fluid obtained was added at the concentration of 2% based on the medium to an L-shaped incubation tube in which the same yeast extract medium has previously been dispensed and incubated while shaking at 60 rpm at a temperature of 23 to 41° C. for 7 days using a temperature gradient shaker incubator (Advantec Toyo Co. Ltd., Model TN-2148).

Proliferation of the cell in the culture fluid was represented as turbidity (absorbance at 660 nm×dilution magnitude of the culture fluid) for comparison. The saccharide-based erythritol yield was calculated by determining the amounts of glucose remained and erythritol produced in the culture fluid using high performance liquid chromatography. *Moniliella tomentosa* var. *pollinis* (CBS461.67) and a strain of Aureobasidium sp (SN-G42, FERM P-8940) were also subjected to the examination for cell proliferation similarly as described above. The results are shown in Table 1.

TABLE 1

| Cultivation temperature | Variant | Turbidity Parent strain | Moniliella strain | Aureobasidium strain |
|---|---|---|---|---|
| 23 | 51.8(12.3%) | 82.4(8.7%) | 95.5 | 100.2 |
| 28 | 56.9(15.1%) | 95.7(16.9%) | 96.0 | 110.7 |
| 32 | 55.8(26.0%) | 87.8(23.2%) | 72.3 | 126.7 |
| 35 | 51.5(41.5%) | 97.3(36.2%) | 66.3 | 120.4 |
| 37 | 45.9(43.3%) | 97.7(37.3%) | 24.9 | 93.0 |
| 39 | 51.4(30.9%) | 88.0(38.5%) | — | 13.6 |
| 41 | 12.6(10.1%) | 39.2(16.1%) | — | — |

Values in brackets represent saccharide-based erythritol yields.

As shown in Table 1, the variant of the present invention (FERM BP-5773) exhibited far lower cell proliferation when compared with other three strains. Thus, the optimum temperature range for erythritol production in the variant was 35 to 37° C., with the turbidity being 45.9 to 51.1. In contrast, the optimum temperature range for erythritol production in the parent strain (CBS649.66) was 35 to 39° C., with the tubidity being 88.0 to 97.7, which was almost two times greater, indicating the cell mass which was about two times that of the variant.

In addition, the optimum temperature range in *Moniliella tomentosa* var. *pollinis* strain (CBS461.67) was 27 to 32° C. (Japanese Patent Publication 6-30592), with the turbidity at 32° C. being 72.3, which was almost 1.5 times that of the variant. The optimum temperature range in Aureobasidium strain SN-G42 (FERM P-8940) was 35 to 37° C. (Japanese Patent Publication 4-11189 and ibid. 4-635), with the turbidity being 93.0 to 120.4, which was almost two times or more that of the variant. Example 4 (Comparison of erythritol production based on saccharide concentration)

The variant (FERM BP-5773) and the parent strain (CBS649.66) were compared with regard to erythritol production when cultivated at various saccharide concentrations. Each strain was inoculated to an yeast extract medium (containing 30 w/v % glucose and 1 w/v % of yeast extract) and cultivated at 35° C. for 3 days while shaking.

Then, the culture fluid was added at the concentration of 2% based on the medium to a saccharide concentration test medium, i.e., an yeast extract medium whose glucose concentration has been adjusted to 20 to 60 w/v % (the amount of the yeast extract added to the medium was adjusted to obtain a constant C/N ratio), which has previously been dispensed in a conical flask, and cultivated at 35° C. while shaking at 220 rpm. The cultivation was terminated at the time point when almost all glucose in the medium was consumed. While the cultivation period ranged from 5 to 11 days depending on the concentration, cultivation in 60% glucose group was discontinued in mid course because an increase in the saccharide-based erythritol yield was no longer observed even though glucose still remained in the culture fluids both of the variant and the parent strain. The cultivation period in the variant in the groups of 30 to 50% glucose was equal to or shorter than that in the parent strain. The results are shown in Table 2.

TABLE 2

| Glucose (w/v %) | Variant | | Parent strain | |
| --- | --- | --- | --- | --- |
| | Turbidity | Saccharide-based erythritol yield (%) | Turbidity | Saccharide-based erythritol yield (%) |
| 20 | 50.3 | 34.5 | 75.9 | 39.7 |
| 30 | 67.4 | 40.9 | 100.8 | 38.2 |
| 40 | 76.4 | 45.5 | 103.8 | 38.9 |
| 50 | 66.9 | 39.2 | 93.6 | 34.8 |
| 60 | 63.9 | 27.5 | 62.6 | 17.8 |

As evident from the above table, both of the variant and the parent strain exhibited high saccharide-based erythritol yields at the concentration of glucose ranging from 20 to 50 w/v %. At a glucose concentration as high as 30 w/v % or higher, the variant (FERM BP-5773) exhibited a higher saccharide-based erythritol yield when compared with parent strain (CBS649.66), showing better results. The variant also exhibited a lower turbidity when compared with the parent strain, indicating the less cell proliferation.

EXAMPLE 5
(Comparison of erythritol production depending on types of saccharides)

An yeast extract medium was used as a basal medium while being supplemented with various saccharides (glucose, fructose, maltose, sucrose and used to cultivate the variant (FERM BP-5773) and the parent strain (CBS649.66). Thus, the variant of the present invention or the parent strain was inoculated to an yeast extract medium (containing 30 w/v % of glucose and 1 w/v % of yeast extract) and cultivated at 35° C. for 3 days while shaking.

Then, the culture fluid obtained was inoculated at the concentration of 0.25% based on the medium to a medium formulated by adding each saccharide to an yeast extract medium as a basal medium (containing 40 w/v % of saccharide and 1.3 w/v % of yeast extract) and the shaking in a conical flask was continued at 35° C. for 7 days, after which erythritol contained in the culture fluid was quantified. The results are shown in Table 3-1 and Table 3-2.

TABLE 3-1

| | Variant (unit: g/L) | | | |
| --- | --- | --- | --- | --- |
| | Glucose | Fructose | Maltose | Sucrose |
| Erythritol | 180.2 | 185.0 | 68.2 | 147.6 |
| Glycerin | 18.0 | 3.4 | 0 | 0 |
| Ribitol | 4.5 | 10.9 | 0 | 4.4 |
| Ethanol | 0 | 0 | 0 | 0 |

TABLE 3-2

| | Parent strain (unit: g/L) | | | |
| --- | --- | --- | --- | --- |
| | Glucose | Fructose | Maltose | Sucrose |
| Erythritol | 149.9 | 136.5 | 51.8 | 139.1 |
| Glycerin | 18.3 | 16.0 | 0 | 0 |
| Ribitol | 4.2 | 17.7 | 0 | 0 |
| Ethanol | 0 | 0 | 0 | 0 |

As evident from Table 3-1 and Table 3-2, both of the variant and the parent strain produced large amounts of erythritol and small or slight amounts of glycerin and ribitol from glucose, fructose and sucrose. Production of erythritol from maltose was small. Particularly, the variant produced erythritol in the largest amounts from glucose and fructose, with the saccharide-based yields being 45.1% and 46.3%, respectively.

EXAMPLE 6
(Effect of pH)

The variant (FERM BP-5773) and the parent strain (CBS649.66) were cultivated to compare the pH in culture medium. Thus, each strain was inoculated to an yeast extract medium (containing 30 w/v % of glucose and 1 w/v % of yeast extract), which was then cultivated at 35° C. for 3 days while shaking. Subsequently, the culture fluid obtained was inoculated (0.2% based on the medium) to a medium adjusted to pH 3.0 to 5.0 with hydrochloric acid and cultivated in a mini-jar fermenter (Able Co. Ltd., Model DPC-2) at 35° C. for 7 days while stirring at 450 rpm. The pH of the medium was kept at the initial pH as far as possible until the end of the cultivation. The results (turbidity and saccharide-based erythritol yield of the culture fluid at each pH) are shown in Table 4.

TABLE 4

| | Variant | | Parent strain | |
| --- | --- | --- | --- | --- |
| pH | Turbidity | Saccharide-based erythritol yield (%) | Turbidity | Saccharide-based erythritol yield (%) |
| 3.0 | 70.5 | 44.6 | 87.0 | 34.0 |
| 3.5 | 71.1 | 46.2 | 118.3 | 34.4 |
| 4.0 | 80.2 | 46.8 | 131.4 | 35.3 |
| 4.5 | 90.7 | 37.9 | 171.7 | 32.5 |
| 5.0 | 93.9 | 34.2 | 191.5 | 31.5 |

As evident from the above table, the variant (FERM BP-5773) exhibited the cell mass (turbidity) smaller than, and, especially at pH 4.5 or higher, about a half of, that of the parent strain (CBS649.66).

INDUSTRIAL APPLICABILITY

The variant of the present invention is characterized by a higher saccharide resistance, a higher erythritol yield and a smaller cell mass produced, when compared with the parent strain. Accordingly, it is suitable for the production of erythritol in an industrial scale.

In addition, since the method for producing erythritol according to the present invention enables the culture of the strain employed in a medium containing a saccharide at a high concentration, erythritol can be produced efficiently at a low cost.

We claim:

1. A mutant strain of *Trichosporonoides oedocephalis* whose saccharide-based erythritol yield, at a saccharide concentration of 30 w/v % or higher but less than 60 w/v %, is higher than that in its parent strain and whose cell biomass cultured is less than that of its parent strain.

2. The mutant strain according to claim 1 wherein said mutant strain is *Trichosporonoides oedocephalis* TO-241-14 (FERM BP-5773).

* * * * *